(12) United States Patent
Strand

(10) Patent No.: US 6,786,893 B2
(45) Date of Patent: Sep. 7, 2004

(54) ELASTIC ABSORBENT ARTICLE

(75) Inventor: Lina Strand, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/985,255

(22) Filed: Nov. 2, 2001

(65) Prior Publication Data

US 2002/0052589 A1 May 2, 2002

Related U.S. Application Data

(60) Provisional application No. 60/144,921, filed on Nov. 2, 2000.

(51) Int. Cl.[7] .............................. A61F 13/15; A61F 13/20
(52) U.S. Cl. ............................. 604/385.04; 604/385.03; 604/385.17; 604/385.22; 604/387
(58) Field of Search ................................. 604/365, 366, 604/361, 380, 383, 385.01, 385.03, 385.04, 385.101, 385.08, 385.17, 385.22, 385.24, 387

(56) References Cited

U.S. PATENT DOCUMENTS

| | | |
|---|---|---|
| 3,929,135 A | 12/1975 | Thompson |
| 4,534,769 A | 8/1985 | De Jonckheere et al. |
| 4,673,403 A | 6/1987 | Lassen et al. |
| 5,218,208 A * | 6/1993 | Augier et al. .......... 250/363.02 |
| 5,591,149 A * | 1/1997 | Cree et al. .................. 604/378 |
| 5,658,269 A | 8/1997 | Osborn, III et al. |
| 5,713,884 A | 2/1998 | Osborn, III et al. |
| 5,807,362 A * | 9/1998 | Serbiak et al. .............. 604/361 |
| 6,129,720 A | 10/2000 | Blenke et al. |
| 6,503,233 B1 * | 1/2003 | Chen et al. ............ 604/385.01 |

FOREIGN PATENT DOCUMENTS

| | | |
|---|---|---|
| WO | 94/10956 | 5/1994 |
| WO | 95/17148 | 6/1995 |
| WO | 96/19169 | 6/1996 |

* cited by examiner

Primary Examiner—Karin Reichle
(74) Attorney, Agent, or Firm—Burns, Doane, Swecker & Mathis, L.L.P.

(57) ABSTRACT

An elastic absorbent article such as a sanitary towel, a panty liner or an incontinence pad includes an inner layer and an outer layer which are elastic and an intermediate absorption body which is non-elastic. The absorption body is connected to at least one of the inner and outer layers only in a central and small region and in that the region is visibly marked on the inner layer.

9 Claims, 4 Drawing Sheets

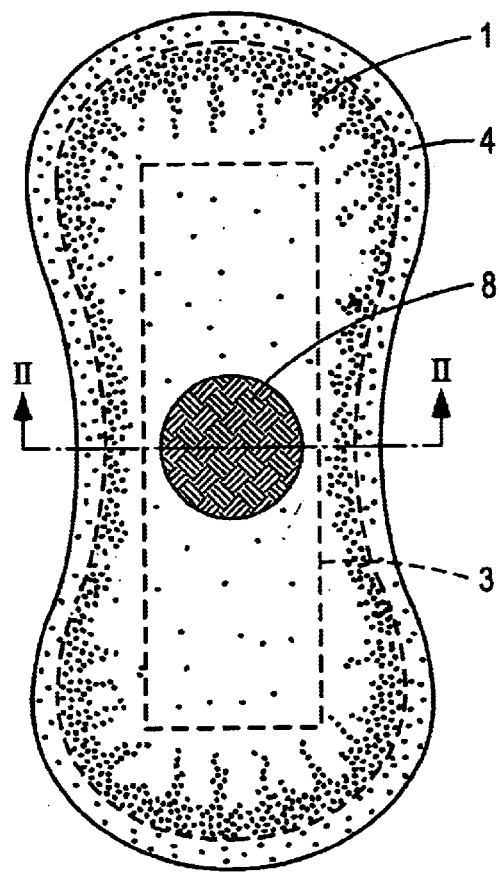
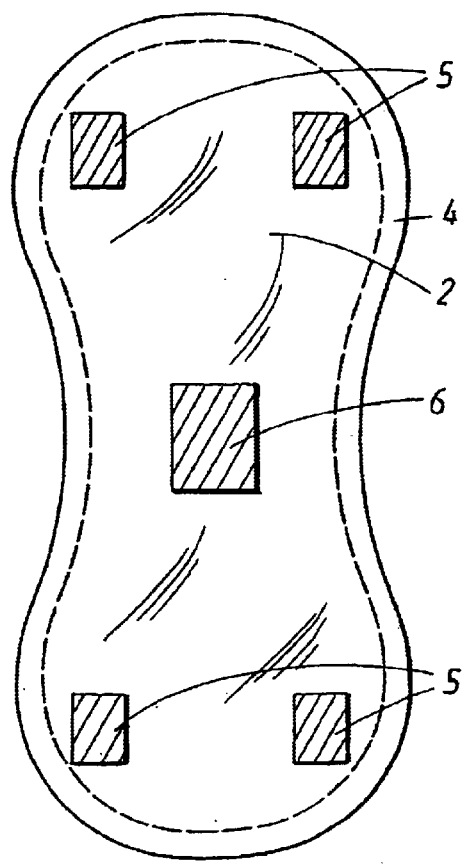
FIG. 1
FIG. 3
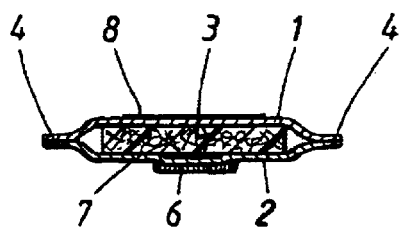
FIG. 2

ELASTIC ABSORBENT ARTICLE

This application claims benefit to U.S. Provisional Application No. 60/144,921, filed on Nov. 2, 2000; the entire content of which is hereby incorporated by reference.

FIELD OF THE INVENTION

The present invention relates to an elastic absorbent article such as a sanitary towel, a panty liner or an incontinence pad, intended to be placed in the crotch region of an undergarment, which article has a longitudinal direction and a transverse direction and comprises a liquid-permeable inner layer and a liquid-impermeable outer layer and an absorption body enclosed between the said layers, in addition to which the article incorporates fastening means for securing the article in the undergarment.

BACKGROUND OF THE INVENTION

Conventional sanitary towels and panty liners, and incontinence pads in the same order of magnitude, are provided with fastening means for holding the article in place in the undergarments of the user.

A known problem is that undergarments are stretched and can also be locally displaced under the movements which occur in the use of the undergarment and that the sanitary towel is in this case dragged along by the garment and displaced from its position directly in front of the genitalia of the user. This is a common cause of leakage of body fluid from sanitary towels in the lateral direction.

Sanitary towels of conventional type are not stretchable or elastic and, apart from being unable to imitate the movements of the undergarment, are not flexible with the body and can be felt to be stiff and uncomfortable for the user.

Undergarments are felt by the majority of users to be comfortable and flexible. It has been proposed to design sanitary towels such that they are stretchable and, suitably, also elastic, so that they can imitate the movements of the user and the undergarment and remain in the intended position.

In U.S. Pat. No. 5,713,884, for example, sanitary towels are described which are stretchable and, preferably, also elastic.

The stretchability of the sanitary towel should suitably correspond to the stretchability or elasticity of the undergarment. It has been shown that ca. 20% stretchability is sufficient for undergarments to allow them to imitate body movements made by a user. This is also discussed in U.S. Pat. No. 5,713,884.

In the said publication it is stated that, suitably, all materials included in the sanitary towel shall be stretchable and preferably also elastic. Yet an illustrative embodiment is also mentioned in passing, in which the included absorbent material is not stretchable, though it is stated, at the same time, that this embodiment is not preferred.

It is possible to produce a sanitary towel which, owing to its elasticity, can adapt to the movements which occur in the undergarments of the user.

On the other hand, it is difficult to find elastic materials which have sufficient absorbency and liquid holding capacity and other properties demanded of present-day absorption materials. It is, however, easier to find inner layers and outer layers which are elastic and which, at the same time, can manage their respective functions, such as permeability and dryness for the inner layer and liquid-tightness for the outer layer.

By dropping the requirement that the absorption core also be elastic, there is no need to seek special absorption materials which are elastic and which, at the same time, can meet the tough capacity requirements which are placed on absorption materials in present-day sanitary towels. It is instead possible to make an arbitrary choice from all available absorption materials.

A problem which has not hitherto received attention is the risk that a non-elastic absorption core might easily end up in the wrong position when exposed to forces arising from the elastic outer layers when these are elongated and fastened in the undergarment of the user. When forces are applied and the outer layers of the product (sanitary towel) are lengthened as the towel is positioned, it is very important for the user to know where the absorption body is placed in the product (sanitary towel). In other words, it is important to ensure that the absorption body of the towel ends up directly in front of the genitalia of the user.

SUMMARY OF THE INVENTION

As a result of the present invention, an elastic absorbent article of the type described in the introduction has been achieved, which article essentially eliminates the problems described above.

An absorbent article according to the invention is characterized in that the inner layer and the outer layer are elastic and in that the intermediate absorption body is non-elastic, in that the inner layer and the outer layer extend beyond the absorption body in the lateral and longitudinal directions and are mutually joined there, in that the absorption body is connected to at least one of the said inner and outer layers only in a central and small region and in that the region is visibly marked on the liquid-permeable layer.

Owing to the visible marking, the central part of the sanitary towel, and hence the absorption body, can be optimally placed in the undergarment so that the said central region ends up directly in front of the genitalia of the user.

Expediently, the marking is constituted by a color marking or pattern stamp. Other types of markings are naturally possible. The essential point is that the marking is easily visible.

The fastening means are constituted by bonding agent coatings applied at separate locations on the liquid-impermeable layer. This is important in order for the inner and outer layers of the sanitary towel to be elastically stretchable over intermediate regions which have no coating of bonding agent. Expediently, bonding agent coatings are applied in the four corner regions of the article.

As stated above, it is essential that the central, marked region of the sanitary towel ends up in the correct position.

According to a suitable embodiment of the invention, one region of the bonding agent coating is therefore also applied right opposite of the marking.

According to a further embodiment of the invention, wings are arranged to extend beyond the outer and inner layers in the lateral direction. The wings are provided with fastening means devices and are intended to be folded around the edge of the crotch section of the undergarment and fastened to the outside thereof when the sanitary towel is positioned.

One way of reducing the risk of edge leakage caused by deformation of the product during use is to provide the product with a pre-formed, anatomically matched elevation, which is intended to be placed against the genitalia of the user when the product is positioned. The intention is also, of course, that the product, with its elevation, will remain in the applied position during use. This is facilitated if the elevation or hump is designed such that it is rigid under normal usage stresses. According to a suitable embodiment, the product according to the invention is therefore characterized in that the absorbent body is convex in the direction of the liquid-permeable inner layer which is facing the user during use of the product and in that the marking is applied to the inner layer substantially on the top of the convex surface formed.

If the absorbent body is relatively rigid in comparison to the inner and the outer layer, the absorption body, since it is fastened to the inner and/or the outer layer only in a central region, will otherwise "float freely" between the inner and outer layers. In embodiments in which the absorption body has an extent such that it is relatively wide and approaches in the lateral direction the bound-together outer edges of the inner and outer layers, the absorption body is suitably rounded in the corners in order to prevent the free corner sections of the absorption body from catching in the bound-together edge sections of the inner and outer layers.

BRIEF DESCRIPTION OF THE FIGURES

The invention will be described in greater detail below with reference to illustrative embodiments shown in the appended drawings, in which:

FIG. 1 shows a sanitary towel according to a first embodiment, viewed from the side which is intended to be facing the user when the sanitary towel is in use;

FIG. 2 shows a cross section along the line II—II in FIG. 1;

FIG. 3 shows the sanitary towel according to FIG. 1, viewed from the side which is facing away from the user when the towel is in use;

DETAILED DESCRIPTION OF THE INVENTION

Figure 4:
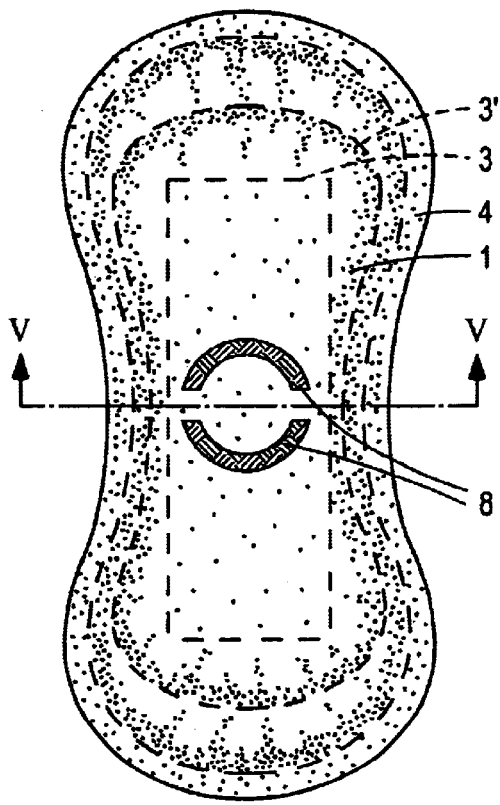
FIG. 4 shows a sanitary towel according to a second embodiment, viewed from the side which is intended to be facing the user when the sanitary towel is in use.

The sanitary towel shown in FIGS. 1–3 has an inner layer 1 of liquid-permeable material and an outer layer of liquid-impermeable material. The outer layer and the inner layer are formed from elastic material. By elastic materials is here meant materials which can stretch in the order of magnitude of at least 20%, under normally occurring stresses and which revert substantially to their original length once the load is relieved.

Between the inner layer 1 and the outer layer 2, a non-elastic absorbent body 3 is placed. By non-elastic is here meant that the absorbent body does not stretch at least not elastically under loads which normally occur when the sanitary towel is used. The inner and outer layers extend beyond the absorbent body 3 in the lateral and longitudinal directions and are mutually joined there along an edge section 4.

The outer layer 2 is intended to be fastened to the inside of the undergarment (not shown) of the user by means of bonding agent coatings 5, one at each corner, as can be seen from FIG. 3. A bonding agent coating 6 is arranged in the center of the liquid-tight outer layer. The said bonding agent coatings are suitably constituted by pressure-sensitive hot-melt adhesive, as it is known. Once the towel is fixed in the undergarment, the inner and outer layers will be stretched and elastically carried along by the undergarment as it moves, which movements, in turn, imitate the body movements of the user.

In the region right opposite of the bonding agent coating 6, the absorbent body 3 is connected to the inside of the liquid-impermeable outer layer 2 by means of a central bonding agent coating 7 of essentially the same extent as the bonding agent coating 6 on the outside of the outer layer.

On the inside of the liquid-permeable layer 1 there is arranged a marking 8, which is visible as the product is positioned and, in connection herewith, is intended to be placed directly in front of the genitalia of the user.

When a user wearing a sanitary towel of the type described in FIGS. 1–3, fitted in an undergarment, moves, the inner and outer layers of the sanitary towel are carried along by the undergarment whenever this is stretched or locally displaced, as has been mentioned above. In the region right opposite of and around the genitalia of the user, the undergarments of the user are essentially unaffected under normal body movements. Since the non-elastic absorbent body 3 is connected to the outer layer 2 by means of the bonding agent coating 7 only in a central region, the absorbent body will be essentially unaffected by tensile stresses arising in the elastic inner and outer layers 1 and 2 respectively. This relationship is exploited in the product according to the invention by virtue of the fact that the absorbent body is placed optimally directly in front of the genitalia of the user when the towel is positioned, using the visible marking 8. As has been described above, this is situated, right opposite of the central bonding agent coating 7, which constitutes the sole anchorage of the absorbent body in the outer layer 2. The absorbent body 3 will therefore remain in optimal position throughout the use of the towel, essentially regardless of the movements of the user.

The wet point of the sanitary towel, as it is known, will therefore coincide with, alternatively be enclosed by, the marking 8 on the inner layer.

The bonding agent coating 6, which is applied to the outside of the liquid-impermeable layer 2, is placed right opposite of the bonding agent coating 7, which, in turn, is situated right opposite of the marking 8 on the liquid-permeable layer 1.

When a user places the sanitary towel with the marking 8 right opposite of her genitalia, the connection, the bonding agent coating 7, thus ends up between the absorbent body 3 and the casing of the sanitary towel right opposite of the genitalia of the user. The bonding agent coating 6 is fastened to the inside of the crotch section of an undergarment in a region of the undergarment which is not affected by movements of the user. The bonding agent coatings 5 in the four corners of the sanitary towel are fastened to an undergarment in regions thereof which can be carried along when the user moves.

Undergarments are made from materials which are flexible and comfortable for the user. The casing of the sanitary towel, which is formed by the inner layer 1 and the outer layer 2, is formed from elastic materials of such elasticity that the casing imitates the movements of the undergarment under the forces which normally occur whilst the undergarment and the sanitary towel are in use. The adhesion between the adhesive coatings 5 and the undergarment of the user is sufficient for the sanitary towel not to come loose from the undergarment but to be carried along with its movements.

The advantage of an elastic towel is that the towel is able to stretch instead of being pulled out of its optimal usage position, i.e. a position in which the absorbent body is situated directly in front of the genitalia of the user.

Since the marking 8 on the sanitary towel is placed in the undergarment such that the marking is situated right opposite of the genitalia of the user when the sanitary towel is in use, i.e. in a region of the undergarment which is essentially unaffected by movements of the user, the absorbent body, which is secured in the casing right opposite of the marking 8 by means of the bonding agent coating, will remain in optimal position right opposite of the genitalia of the user while the sanitary towel is used.

The fact that the casing of the sanitary towel can be elastically carried along by the undergarment, under movements of the user, without any effect upon the sanitary towel in the region right opposite of the marking means that the absorbent body 3 will remain in optimal position throughout the use of the sanitary towel.

In the case of conventional, non-elastic sanitary towels, the absorbent body is carried along whenever the undergarment imitates movements of the body and there is a risk of possible leakage resulting from the absorbent body of the sanitary towel ending up at an oblique angle in relation to the genitalia of the user.

When the casing is elastic and the absorbent body is non-elastic, it is important for the absorbent body to be placed in the correct position when the sanitary towel is positioned.

If a sanitary towel of the type which is shown in FIGS. 1–3 is wrongly positioned so that the region of the bonding agent coating 7 ends up right opposite of a region on the undergarment which can be displaced under movements of the user, there is a risk of the absorbent body being pulled further from its optimal position, giving rise to an obvious risk of leakage.

The securement of the non-elastic absorbent body in a small, delimited region by means of the bonding agent coating 7 is essential. If the absorption body were to be connected to the elastic casing by means of a fastening line extending along the length of the absorbent body, as is described in U.S. Pat. No. 4,534,769, the absorbent body would be acted on by tensile stresses arising in the undergarment and there would be a high risk of the absorbent body of the sanitary towel being pulled out of its optimal position right opposite of the genitalia of the user, with an attendant risk of leakage.

In the design according to FIGS. 1–3, the absorbent body can "float freely" within the casing over the main part of its surface and is only secured in a region which is intended to be placed right opposite of the genitalia of the user while the sanitary towel is used, i.e. in a region in which the undergarment is not displaced.

A suitable elastic inner layer 1 can be formed from a plurality of different materials including, but not limited to, fiber (non-woven) fabrics, perforated plastic films, porous foam and plastic gauze.

Suitable fiber fabrics can consist of one type of fibers or a combination of fibers, such as fibers of polyester, polypropylene, polyethylene, nylon and rayon.

An inner layer 1 in the form of perforated plastic film offering reduced re-wetting is known from a large number of patents. An early example of perforated plastic films is described in U.S. Pat. No. 3,929,135.

The elasticity in a plastic film is determined by a choice of plastic material and/or by controlling the elasticity in a plastic film by means of the configuration of the perforation. The inner layer can obviously consist of a multi-layered laminate, at least one layer of which is elastic.

The outer layer 3 is liquid-impermeable and can be constituted, for example, by a polyethylene plastic film having suitable elastic properties. The outer layer should have a stretchability of more than 20% under the loads which normally occur on a sanitary towel secured in an undergarment. The outer layer can also be formed from an elastic, hydrophobic non-woven fabric. The outer layer can also be constituted by a laminate, such as a very thin plastic film, in combination with an elastic non-woven fabric.

The choice of material in the inner layer and outer layer is not critical. The essential point is that the inner layer is liquid-permeable and the outer layer is liquid-impermeable and that the two layers are elastically stretchable so that they are flexible to conventional undergarments.

The fact that the absorption body in the sanitary towel is able to be non-elastic has the fundamental advantage that it is possible to make an arbitrary choice of absorption body from absorption bodies available on the market, without any compromises for them having to be elastic.

A suitable absorbent material for the absorption body 6 in FIGS. 1–3 is the material described in WO 94/10956. This material is constituted by a dry-formed, fiber layer with a high density and is used directly in an absorbent article without it first being defibrated. Another similar material, which has especially suitable blood-absorption properties, is described in WO 94/10953. The materials described in the two latter publications are relatively stiff and have good capacity to withstand pressure deformations. The material can be softened by mechanical treatment. The materials described in the latter publications have good absorbency. The materials swell in the direction of thickness during absorption and are thereby able to adapt to space available in the crotch of the user.

The choice of material is not critical. Another example of a suitable absorption material is cellulose fluff material, possibly with the admixture of a highly-absorbent polymer in powder or fiber form.

The marking 8 can be constituted by a color marking. Another example is that the marking having been formed by relief printing. The inner layer 1 can be connected to the absorbent body in the region delimited by the marking and the visible marking can in this case be constituted by a bonding agent coating which is visible through the inner layer 1.

According to another suitable illustrative embodiment, the marking is constituted by a number of visible holes, which, apart from serving as a marking, can be formed to make it easier for liquid to pass into the absorbent body.

Figure 6:
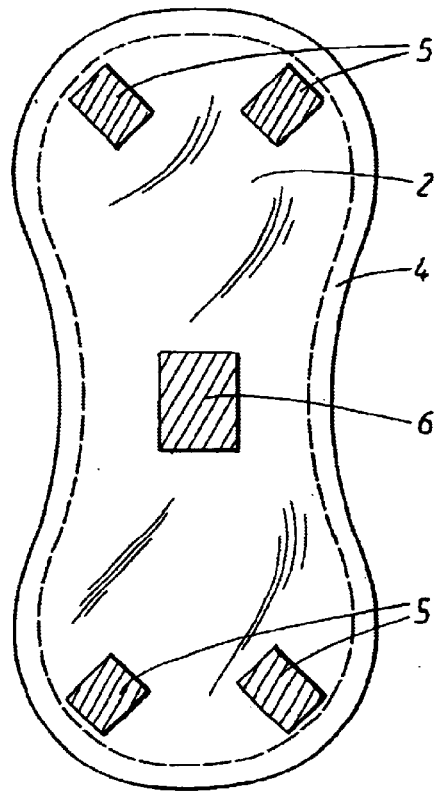
FIG. 6 shows the sanitary towel according to FIG. 4, viewed from the side which is facing away from the user when the towel is in use.
Figure 5:
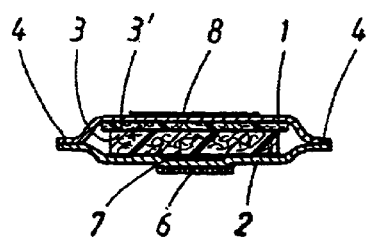
FIG. 5 shows a cross section along the line V—V in FIG. 4.

In the embodiment according to FIGS. 4–6, the details which essentially conform in every respect to corresponding details in the embodiment according to FIGS. 1–3 have been provided with the same reference notations.

In the embodiment according to FIGS. 4–6, the absorbent body consists of a main absorbent body 3, similar to the absorbent body 3 in the embodiment according to FIGS. 1–3, and a substantially hourglass-shaped absorbent layer 3'. This is situated next to the user inside the inner layer 1 and is of softer configuration than the underlying main absorbent body 3.

The hourglass-shaped absorbent layer 3' serves as an insulating layer between the liquid-permeable inner layer 1 and the main absorbent body 3 and has the capacity to rapidly admit liquid to the main absorbent body, which has higher liquid affinity than the hourglass-shaped absorption layer 3'. This can suitably be formed from a low-density, air-laid fiber layer.

The marking 8, which is intended to show where the towel is to be placed, here has the shape of two annular segments, which are arranged on both sides of the wet point of the sanitary towel, as it is known, i.e. the region which is intended to be situated right opposite of the genitalia of the user while the sanitary towel is used. These annular segments can be made visible in a similar manner to the marking 8 which has been described above in connection with FIGS. 1–3.

Since the marking 8 in the embodiment according to FIGS. 4–6 is not situated over the wet point, this marking does not need to be liquid-permeable, which increases the options for the configuration of the marking. The marking 8 in FIG. 4 can be constituted, for example, by a bonding agent on the outside of the inner layer 1, which bonding agent, apart from constituting a marking for the positioning of the sanitary towel, serves as fastening means against the skin of the user in a region around the genitalia of the user.

The bonding agent coatings 5 in the corners of the sanitary towel are somewhat elongated and have here been applied at an oblique angle in order better to absorb tensile stresses from the undergarment of the user.

Figure 7:
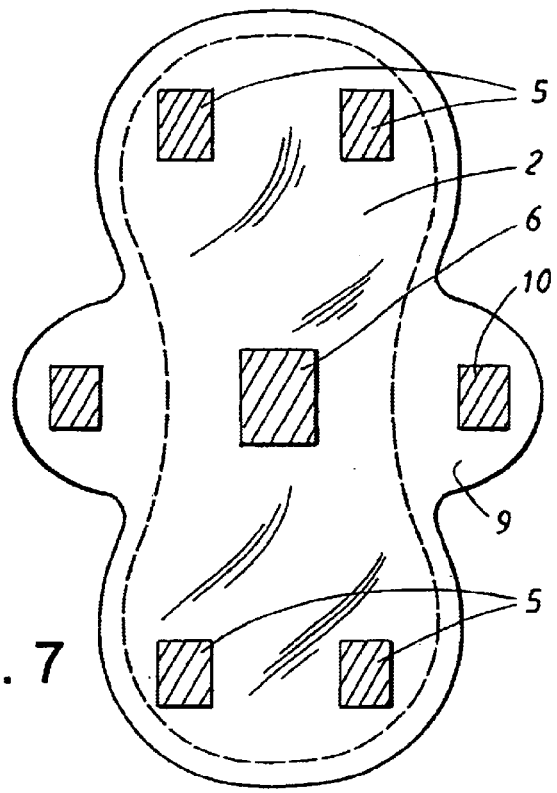
FIG. 7 shows a sanitary towel according to a third embodiment, viewed from the side which is facing away from the user when the towel is in use.
Figure 8:
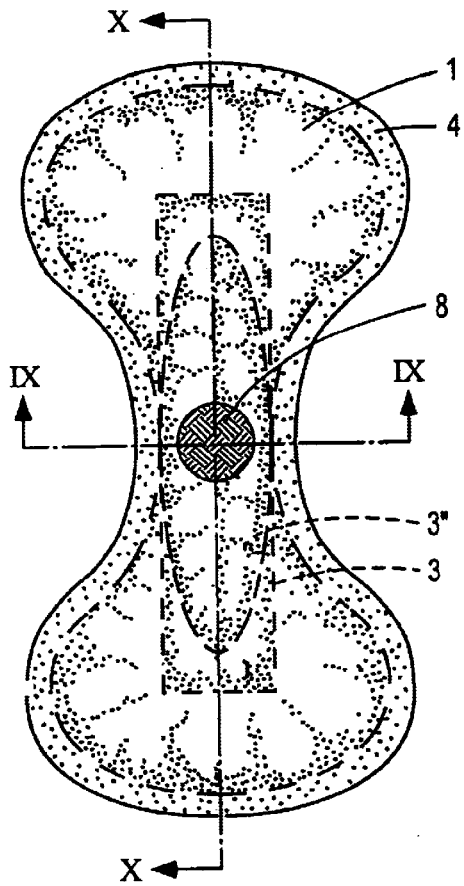
FIG. 8 shows a sanitary towel according to a fourth embodiment, viewed from the side which is facing the user when the towel is in use.
Figure 11:
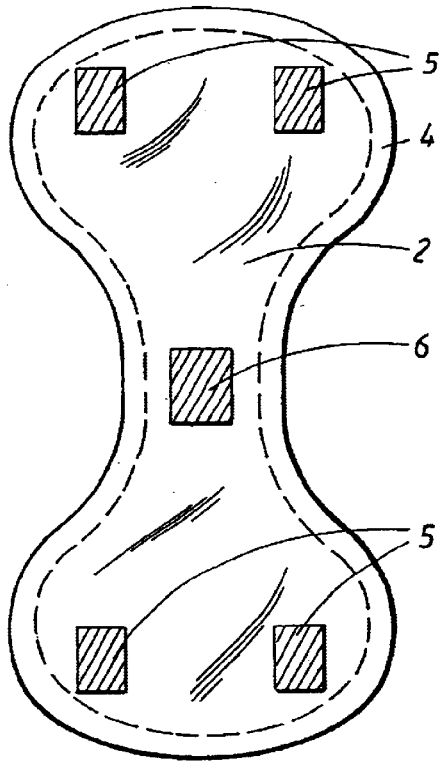
FIG. 11 shows a sanitary towel according to FIG. 8, viewed from the side which is facing away from the user when the towel is in use.
Figure 9:
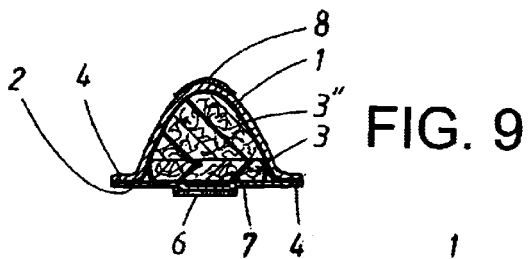
FIG. 9 shows a cross section along the line IX—IX in FIG. 8.
Figure 10:
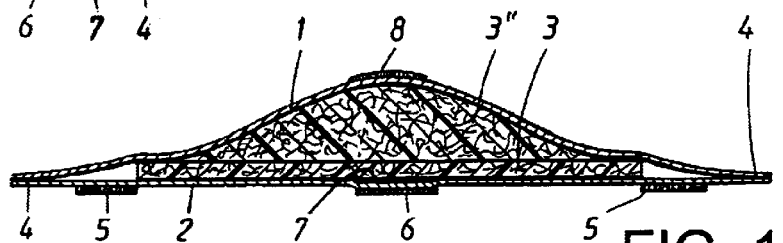
FIG. 10 shows a cross section along the line X—X in FIG. 8.

The embodiment according to FIG. 7 differs from the embodiment according to FIG. 3 only by the fact that the sanitary towel according to FIG. 7 has been provided with wings 9, on which bonding agent coatings 10 are arranged. When the sanitary towel according to FIG. 7 is positioned, the wings are folded around the edge section in the crotch section of the undergarment and the bonding agent coatings 10 are fastened to the outside of the undergarment in the crotch region.

In the embodiment shown in FIGS. 8–11, the details which essentially conform to corresponding details in other illustrative embodiments have been provided with the same reference notations.

The sanitary towel according to FIGS. 8–11 is anatomically configured with a narrower crotch section and with an absorbent body 3, which, in the crotch region, has a bulge 3" which is convex in the direction of the liquid-permeable layer. This convex bulge 3" is designated in professional circles as a hump.

The absorbent body in the embodiment according to FIGS. 8–11 consists of an elongated part 3 and the hump 3". The extent of the latter in the transverse and longitudinal directions can be seen from FIGS. 9 and 10. The marking 8 is applied on the top of the hump 3".

The marking 8 is intended to end up directly in front of the genitalia of the user when the sanitary towel is positioned. The hump is formed in a material which is not essentially deformed when the towel is squeezed in the crotch of the user, but rather the elevation, the hump, of the sanitary towel will bear against the genitalia of the user, so that secreted body fluid is captured as soon as it leaves the body of the user and is absorbed into the sanitary towel instead of running out over its surface.

The hump 3" can be constituted, for example, by a dry-formed fiber layer of the type which is described in WO 94/10956 and which has also been described above in connection with the embodiment according to FIGS. 1–3. The elongated absorption body 3 can also be formed from a dry-formed fiber layer of the above-stated type.

Figure 12:
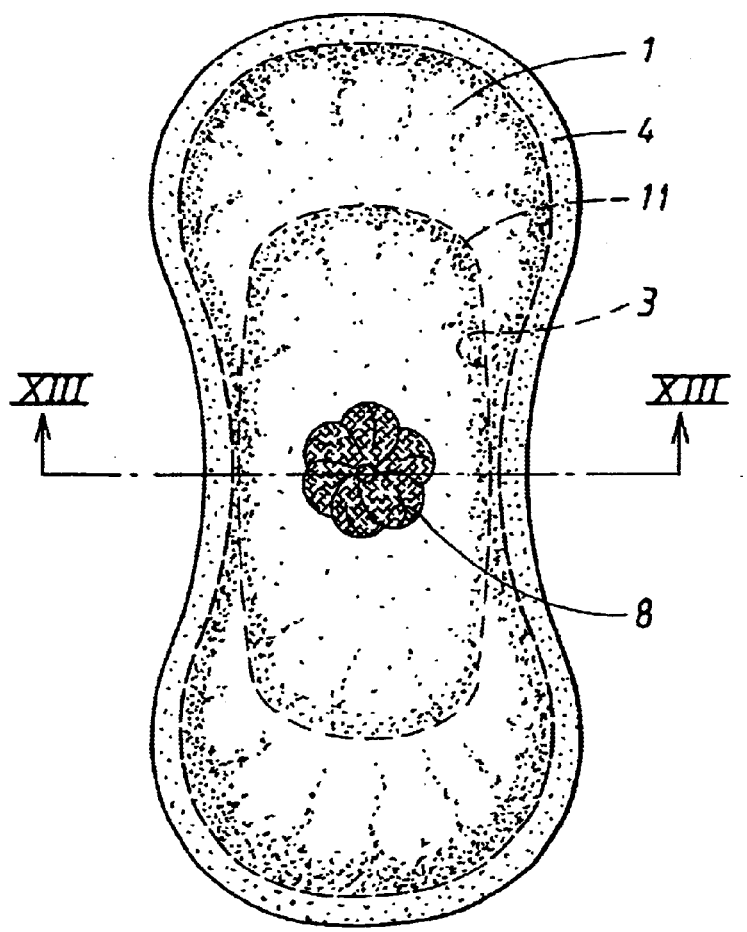
FIG. 12 shows a sanitary towel according to a fifth embodiment, viewed from the side which is facing the user during use.
Figure 13:
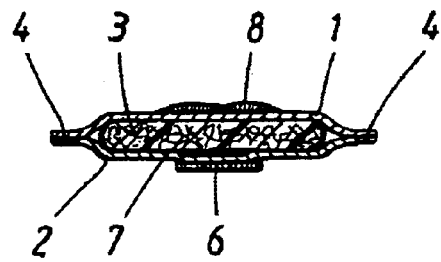
FIG. 13 shows a cross section along the line XIII—XIII in FIG. 12.

In FIGS. 12 and 13, an embodiment which is somewhat modified in relation to the embodiment according to FIGS. 1–3 is shown. The details which conform to corresponding details in the embodiment according to FIGS. 1–3 have been provided with the same reference notations.

The embodiment according to FIGS. 12 and 13 differs primarily from the embodiment according to FIGS. 1–3 by the fact that the absorption body 3 is wider and that the corners 11 of the absorption body are rounded. The corners are rounded in order to prevent these "free-floating" corners from catching against the edge seal 4 inside the casing of the sanitary towel when the user moves and the casing is carried along with the movement of the undergarment.

In the illustrative embodiment shown in FIGS. 12–13, the marking 8 is constituted by a patterned decoration.

The invention is not limited to the above-stated described illustrative embodiments, but rather a plurality of modifications are possible within the scope of the following patent claims.

It has been mentioned above that the liquid-permeable inner layer can be connected with the absorbent core. Such a connection can, dependent on the material in the inner layer and absorbent body, be suitable in order to create contact between the inner layer and the absorbent body and facilitate liquid passing from the inner layer to the absorbent body. When such a connection between the inner layer and the absorbent body exists, the connection is arranged in or around the central, marked region. The connection between inner layer and absorbent core is of course arranged so that it does not block and thereby disturb the inflow of body-liquid from the inner layer to the absorbent core.

The principles, preferred embodiments and manner of use of the present invention have been described in the foregoing specification. However, the invention which is intended to be protected is not to be construed as limited to the particular embodiments described. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. An elastic absorbent article for use as a sanitary towel, a panty liner or an incontinence pad, intended to be placed in a crotch region of an undergarment, which article has a longitudinal direction and a transverse direction, comprising:

liquid-permeable inner layer;

a liquid-impermeable outer layer;

and an absorbent body enclosed between the said inner and outer layers;

fastening means for holding the article in the undergarment;

wherein the inner layer and the outer layer are elastic and the intermediate absorbent body is non-elastic, the inner layer and the outer layer extending beyond the absorbent body in the lateral and longitudinal directions and are mutually joined there along edge sections of the inner layer and the outer layer, the absorbent body being connected to the inside of the liquid-impermeable layer by means of a central bonding agent coating of essentially the same extent as a bonding agent coating on the outside of the outer layer, the central bonding agent coating constituting the sole anchorage of the absorbent body in the outer layer, said bonding agent coating on the outside of the outer layer being fastened to the inside of the crotch section of an undergarment in a region of the undergarment which is not affected by movements of the user, the central bonding agent coating during use is intended to be located right opposite genitalia of a user and the location of the central bonding agent coating being visibly marked with a marking on the liquid-permeable inner layer.

2. The article according to claim 1, wherein the marking is constituted by a color marking or a visible pattern decoration.

3. The article according to claim 1, wherein said fastening means are constituted by bonding agent coatings applied at separate locations on the liquid-impermeable layer.

4. The article according to claim 3, wherein the article has four corner regions and wherein bonding agent coatings are applied in the four corner regions of the article.

5. The article according to claim 1, wherein wings are arranged to extend beyond the outer and inner layers in the lateral direction, which wings are provided with fastening means and are intended to be folded around the edges of the crotch section of the undergarment and fastened to the outside thereof when the article is positioned.

6. The article according to claim 1, wherein the absorbent body is convex in the direction of the liquid-permeable inner layer during use such that the inner layer forms a convex surface of the article and in that the marking is applied to the inner layer substantially on the top of the convex surface formed.

7. The article according to claim 1, wherein the absorbent body has corners and wherein the absorbent body is rounded in the corners in order to prevent the corners of the absorbent body from catching in the mutually joined edge sections of the inner and outer layers.

8. The article according to claim 1, wherein the marking is arranged intermittently or continuously over a second region which is intended to respectively partially or wholly surround but not span genitalia of a user whilst the article is used.

9. The article according to claim 8, wherein the marking is constituted by a bonding agent.

* * * * *